US010019883B2

(12) United States Patent
Peng et al.

(10) Patent No.: US 10,019,883 B2
(45) Date of Patent: Jul. 10, 2018

(54) METHOD FOR MONITORING BREATHING ACTIVITY, ELECTRONIC DEVICE, AND COMPUTER-READABLE STORAGE MEDIUM USING THE SAME

(71) Applicant: HTC Corporation, Taoyuan (TW)

(72) Inventors: De-Zhang Peng, Taoyuan (TW); Huan-Hsin Li, Taoyuan (TW); Ming-Tien Lin, Taoyuan (TW)

(73) Assignee: HTC Corporation, Taoyuan (TW)

( * ) Notice: Subject to any disclaimer, the term of this patent is extended or adjusted under 35 U.S.C. 154(b) by 359 days.

(21) Appl. No.: 15/003,754

(22) Filed: Jan. 21, 2016

(65) Prior Publication Data

US 2017/0213438 A1    Jul. 27, 2017

(51) Int. Cl.
    *G08B 21/06*    (2006.01)
    *A61B 5/08*     (2006.01)
    *A61B 5/113*    (2006.01)
    *A61B 5/00*     (2006.01)
    *G06T 7/00*     (2017.01)
    *G06T 7/20*     (2017.01)
    *A61B 5/11*     (2006.01)

(52) U.S. Cl.
    CPC ............... *G08B 21/06* (2013.01); *A61B 5/08* (2013.01); *A61B 5/0816* (2013.01); *A61B 5/113* (2013.01); *A61B 5/1128* (2013.01); *A61B 5/4806* (2013.01); *A61B 5/7235* (2013.01); *A61B 5/746* (2013.01); *G06T 7/0016* (2013.01); *G06T 7/20* (2013.01); *G06T 2207/10016* (2013.01); *G06T 2207/30196* (2013.01)

(58) Field of Classification Search
    CPC ..... A61B 5/0816; A61B 5/1128; A61B 5/113; A61B 5/4806; A61B 5/7235; A61B 5/746; G06T 7/0012; G06T 7/0016; G06T 7/20; G06T 2207/10016; G06T 2207/10024; G06T 2207/20021; G06T 2207/30196; G08B 21/06
    See application file for complete search history.

(56) References Cited

U.S. PATENT DOCUMENTS

6,335,985 B1 * 1/2002 Sambonsugi ........ G06K 9/3241
                                                        382/190
8,553,940 B2   10/2013 Kirenko et al.
(Continued)

*Primary Examiner* — Edward Park
(74) *Attorney, Agent, or Firm* — JCIPRNET (57) ABSTRACT

The disclosure provides a method, electronic device, and computer-readable storage medium for monitoring breathing activity. The method includes the following steps. A time series of incoming frames of a monitored subject is received and each incoming frame is spitted into multiple blocks, where each block of the time series of incoming frames with a same position forms a time series of incoming blocks. A motion vector of each block is computed and projected onto multiple non-parallel axes to be assigned a sign. The projected motion vectors of each time series of incoming blocks with respect to each axis are respectively merged into a corresponding 1D waveform and converted into a frequency domain, and an observe area is located accordingly. A breathing frequency of the monitored subject corresponding to the observe area is determined and whether or not the monitored subject is breathing abnormally is thereby determined.

20 Claims, 7 Drawing Sheets (56) References Cited

U.S. PATENT DOCUMENTS

| | | | |
|---|---|---|---|
| 2008/0278633 A1* | 11/2008 | Tsoupko-Sitnikov | H04N 5/144 348/699 |
| 2009/0268822 A1* | 10/2009 | Terada | H04N 19/61 375/240.16 |
| 2012/0243733 A1* | 9/2012 | Sawai | G06T 7/2006 382/103 |
| 2013/0289432 A1 | 10/2013 | Van Vugt et al. | |
| 2013/0345568 A1 | 12/2013 | Mestha et al. | |
| 2014/0037166 A1 | 2/2014 | de Haan et al. | |
| 2014/0205165 A1 | 7/2014 | Jeanne et al. | |
| 2014/0236036 A1 | 8/2014 | de Haan et al. | |
| 2014/0276099 A1 | 9/2014 | Kirenko et al. | |
| 2014/0303503 A1 | 10/2014 | Rocque et al. | |

* cited by examiner

| | FV | | | | R45 | | | | | |
|---|---|---|---|---|---|---|---|---|---|---|
| 60Hz | 53Hz | 50Hz | 50Hz | 50Hz | 50Hz | 50Hz | 50Hz | 50Hz | 53Hz | 60Hz — P1 |
| 60Hz | 53Hz | 50Hz | 50Hz | 50Hz | 50Hz | 50Hz | 50Hz | 50Hz | 53Hz | 60Hz — P2 |
| 60Hz | 53Hz | 10Hz | 0.4Hz | 0.4Hz | 0.3Hz | 10Hz | 15Hz | 20Hz | 53Hz | 60Hz |
| 60Hz | 53Hz | 0.1Hz | 0.1Hz | 0.5Hz | 0.5Hz | 0.3Hz | 10Hz | 10Hz | 53Hz | 60Hz |
| 60Hz | 53Hz | 0.1Hz | 0.1Hz | 0.4Hz | 0.3Hz | 0.3Hz | 5Hz | 5Hz | 53Hz | 60Hz |
| 60Hz | 53Hz | 10Hz | 10Hz | 10Hz | 10Hz | 10Hz | 10Hz | 10Hz | 10Hz | 60Hz |
| 60Hz | 53Hz | 5Hz | 5Hz | 5Hz | 5Hz | 5Hz | 5Hz | 5Hz | 5Hz | 60Hz |
| 60Hz | 53Hz | 50Hz | 50Hz | 50Hz | 50Hz | 50Hz | 50Hz | 15Hz | 14Hz | 60Hz |

Pn

FIG. 3E 0-degree axis 45-degree axis 90-degree axis 135-degree axis

METHOD FOR MONITORING BREATHING ACTIVITY, ELECTRONIC DEVICE, AND COMPUTER-READABLE STORAGE MEDIUM USING THE SAME

TECHNICAL FIELD

The disclosure relates to a method for monitoring breathing activity, an electronic device and a computer-readable storage medium using the same.

BACKGROUND

A serious concern for parents of a newborn is a potential death caused by sudden infant death syndrome (SIDS). SIDS is a sudden and unexplained death of an infant less than one year of age. Infant apnea is defined by the American Academy of Pediatrics as "an unexplained episode of cessation of breathing for 20 seconds or longer, or a shorter respiratory pause associated with bradycardia, cyanosis, pallor, and/or marked hypotonia" and is able to cause SIDS. Although studies have failed to solidly confirm a direct association between SIDS and apnea, SIDS can still be thought of as a sleep disorder. A SIDS victim may be unable to control his breathing spontaneously during sleep or to arouse from sleep in response to a breathing problem. Monitoring an infant's breathing activity has thus become crucial in the early detection of potentially fatal conditions.

One approach to monitor the breathing activity is to attach sensors or to put a romper suit with embedded sensors on an infant. Such mechanical approach works by detecting changes in breathing movements in the chest and abdomen of an infant and alerting parents if the movements are abnormal or are not detected for longer than a preset time. However, the aforementioned wearable sensing devices would make direct contact with the infant that tend to cause skin irritation and discomfort. Consequently, there is a need to develop an approach such that sleeping infants could be constantly monitored and protected against the occurrence of SIDS with minimal discomfort.

SUMMARY OF THE DISCLOSURE

Accordingly, the disclosure is directed to a method for monitoring breathing activity, an electronic device and a computer-readable storage medium using the same, which not only obviates a need to put on any wearable device on a monitored subject, but also provides an approach to monitor his breathing activity in a low-cost digital implementation and an efficient manner.

According to one of the exemplary embodiments, the disclosure is directed to a method for monitoring breathing activity. The method is adapted to an electronic device and includes the following steps. First, a time series of incoming frames of a monitored subject is received, and each incoming frame in the time series of incoming frames is split into multiple blocks, where each of the blocks of the time series of incoming frames with a same block position forms a time series of incoming blocks. A motion vector of each of the blocks is computed and projected onto multiple non-parallel axes so as to assign a sign to each of the motion vectors, where the sign is either positive, negative, or zero. The projected motion vectors of each of the time series of incoming blocks with respect to each of the axes are merged into a corresponding one-dimensional (1D) waveform respectively, and the 1D waveforms are converted into a frequency domain. An observe area associated with the monitored subject in the time series of incoming frames is located according to the converted 1D waveforms. A breathing frequency of the monitored subject corresponding to the observe area is determined, and whether or not the monitored subject is breathing abnormally is thereby determined.

According to one of the exemplary embodiments, the disclosure is directed to an electronic device. The electronic device includes a memory and a processor, where the processor is coupled to the memory. The memory is configured to record multiple modules. The processor is configured to access and execute the modules recorded in the memory. The modules includes an image receiving module, an image processing module, a motion vector processing module, a waveform processing module, an observe area locating module, and a breathing frequency processing module. The image receiving module receives a time series of incoming frames of a monitored subject. The image processing module splits each incoming frame in the time series of incoming frames into multiple blocks, where each of the blocks of the time series of incoming frames with a same block position forms a time series of incoming blocks. The motion vector processing module computes and projects a motion vector of each of the blocks onto multiple non-parallel axes so as to assign a sign to each of the motion vectors, where the sign is either positive, negative, or zero. The waveform processing module merges the projected motion vectors of each of the time series of incoming blocks with respect to each of the axes respectively into a corresponding 1D waveform and converts the 1D waveforms into a frequency domain. The observe area locating module locates an observe area associated with the monitored subject in the time series of incoming frames according to the converted 1D waveforms. The breathing frequency processing module determines a breathing frequency of the monitored subject corresponding to the observe area and thereby determines whether or not the monitored subject is breathing abnormally according to the breathing frequency of the monitored subject.

According to one of exemplary embodiments, the disclosure is also directed to a non-transitory computer-readable storage medium, which records computer program to be loaded into an electronic device to execute the steps of the aforementioned method. The computer program is composed of a plurality of program instructions (for example, an organization chart, establishing program instruction, a table approving program instruction, a setting program instruction, and a deployment program instruction, etc.), and these program instructions are loaded into the electronic device and executed by the same to accomplish various steps of the method for monitoring breathing activity.

In view of the aforementioned descriptions, the disclosure provides an image-based technique to monitor breathing activity of a subject through frequency analysis on an input video sequence. The disclosure not only obviates a need to put on any wearable device on the monitored subject, but also provides an approach to monitor his breathing activity in a low-cost digital implementation and an efficient manner.

In order to make the aforementioned features and advantages of the present disclosure comprehensible, preferred embodiments accompanied with figures are described in detail below. It is to be understood that both the foregoing general description and the following detailed description are exemplary, and are intended to provide further explanation of the disclosure as claimed.

It should be understood, however, that this summary may not contain all of the aspect and embodiments of the present disclosure and is therefore not meant to be limiting or restrictive in any manner. Also the present disclosure would include improvements and modifications which are obvious to one skilled in the art.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

To make the above features and advantages of the application more comprehensible, several embodiments accompanied with drawings are described in detail as follows.

DESCRIPTION OF THE EMBODIMENTS

Some embodiments of the disclosure will now be described more fully hereinafter with reference to the accompanying drawings, in which some, but not all embodiments of the application are shown. Indeed, various embodiments of the disclosure may be embodied in many different forms and should not be construed as limited to the embodiments set forth herein; rather, these embodiments are provided so that this disclosure will satisfy applicable legal requirements. Like reference numerals refer to like elements throughout.

Figure 1:
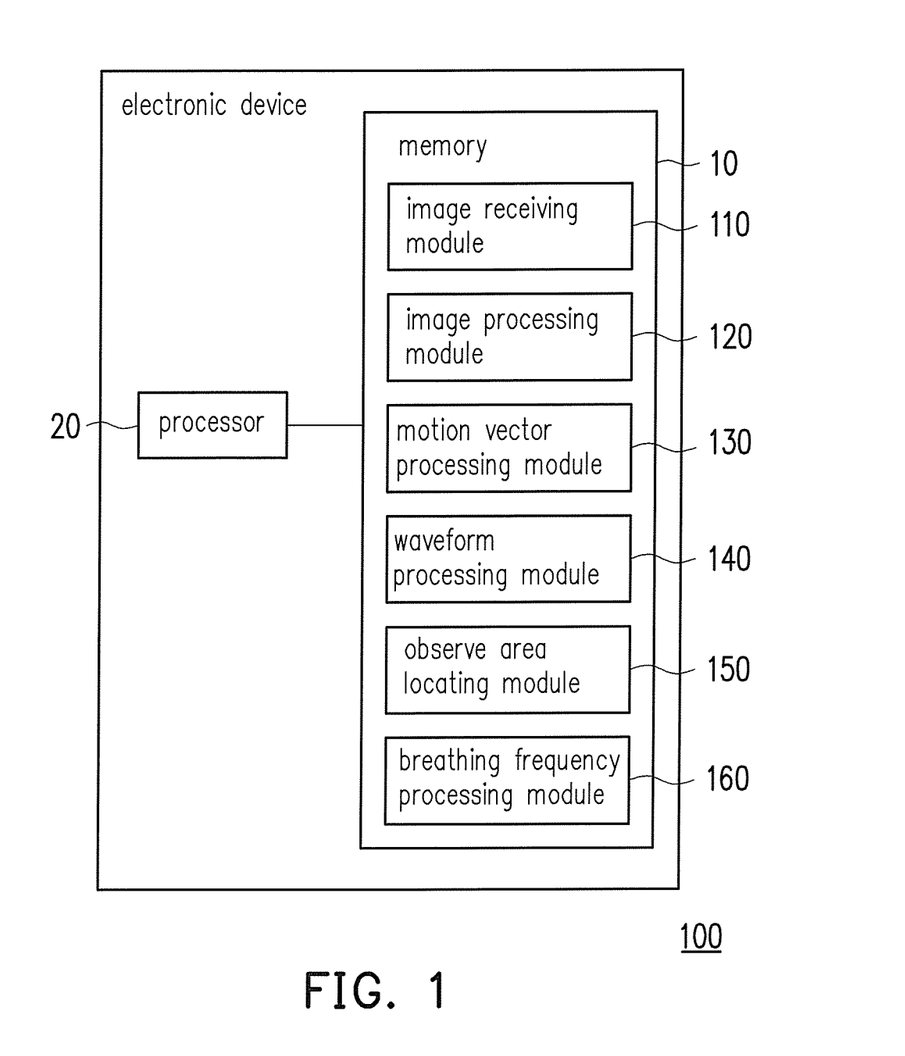
FIG. 1 illustrates an electronic device which utilizes the proposed method from the hardware perspective in accordance with one of the exemplary embodiments of the disclosure.

FIG. 1 illustrates an electronic device which utilizes the proposed method from the hardware perspective in accordance with one of the exemplary embodiments of the disclosure. All components of the electronic device and their configurations are first introduced in FIG. 1. The functionalities of the components are disclosed in more detail in conjunction with FIG. 2.

Referring to FIG. 1, an exemplary electronic device 100 may include a memory 10 and a processor 20, where the processor 20 is coupled to the memory 10. The electronic device 100 may be a personal computer, a laptop computer, a server computer, a tabular computer, a smart phone, a workstation, or other types of computing devices or platforms that is wired or wirelessly connected to an image capturing device such as a digital camera, a digital camcorder, a web camera, a surveillance camera and so forth, or may be built-in in the aforementioned image capturing device. The electronic device 100 could be deployed at home, in a postpartum care center, a nursery room in a hospital for safety purposes.

The memory 10 may include various forms of non-transitory, volatile, and non-volatile memories such as one or a combination of a stationary or mobile random access memory (RAM), a read-only memory (ROM), a flash memory, a hard drive or other similar devices. The memory 10 would store buffered or permanent data such as image data and compiled programming codes used to execute functions of the exemplary electronic device 100. For example, the memory 10 may be configured to record multiple modules executable by the processor 20. The modules may include an image receiving module 110, an image processing module 120, a motion vector processing module 130, a waveform processing module 140, and an observe area locating module 150, and a breathing frequency processing module 160. The modules may be loaded into the processor 20 for monitoring breathing activity of a subject based on a video sequence.

The processor 20 may include one or more of a North Bridge, a South Bridge, a field programmable array (FPGA), a programmable logic device (PLD), an application specific integrated circuit (ASIC), or other similar device or a combination thereof. The processor 140 may also include a central processing unit (CPU), a programmable general purpose or special purpose microprocessor, a digital signal processor (DSP), a graphics processing unit (GPU), an application specific integrated circuit (ASIC), a programmable logic device (PLD), or other similar device or a combination thereof. The processor 20 is capable of accessing and executing the modules recorded in the memory 10 and would be used to perform the method as proposed.

Figure 2:
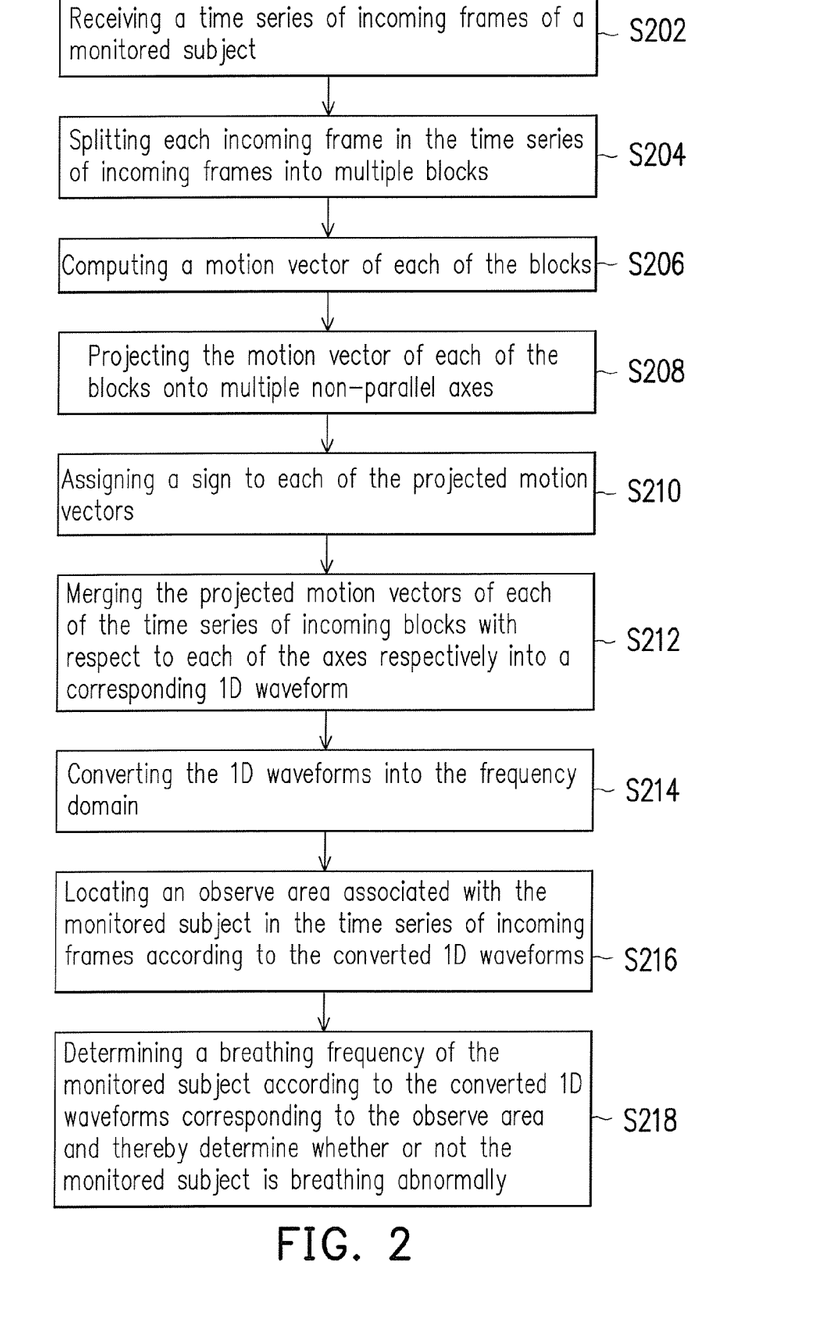
FIG. 2 illustrates a flowchart of a method for monitoring breathing activity in accordance with one of the exemplary embodiments of the disclosure.

FIG. 2 illustrates a flowchart of a method for monitoring breathing activity in accordance with one of the exemplary embodiments of the disclosure. The steps of FIG. 2 could be implemented by the proposed electronic device 100 as illustrated in FIG. 1. In the present embodiment, assume that the electronic device 100 is built-in in an image capturing device.

Referring to FIG. 2, the image receiving module 110 of the electronic device 100 first receives a time series of incoming frames of a monitored subject (Step S202). In other words, an input of an original video frame series in a field of view of the image capturing device would be received by the image receiving module 110. For any particular spot where images are continuously being captured, the monitored subject is assumed to be within the field of view of the image capturing device, and the captured background is assumed to be fixed.

Next, the image processing module 120 splits each incoming frame in the time series of incoming frames into multiple blocks (Step S204). The size of each block could be, for example, 3×3, 9×9, or 17×17 pixels. Each block of the time series of incoming frames with a same block position (i.e., with same pixel coordinates) would form a time series of incoming blocks.

It should be noted that, the received time series of incoming frames could be built in YCbCr color space as provided in most digital video applications. In an embodiment, the image processing module 120 could perform color transformation on the incoming frames to other color spaces.

For example, the incoming frames may be converted into grayscale for an ease of motion vector computation in the follow-up step.

In the present embodiment, the electronic device 100 would keep track on the breathing activity of the monitored subject through frequency analysis on the incoming frames to observe if there exists any abnormal breathing movements. Hence, once the incoming frames are split into blocks and the block size is defined, the motion vector processing module 130 first computes a motion vector of each of the blocks (Step S206) using techniques as readily apparent to a person skilled in the art. For example, the motion vector of each block could be computed by using a block matching algorithm that compares neighboring blocks in two consecutive incoming frames with the minimum mean square error.

The components of a motion vector are an amplitude and a direction at any given time. In order to apply frequency analysis on the incoming frames, the computed motion vectors would be first scaled to time domain data. In other words, the scaled data would be considered as 1D data in the time domain. Thereafter, the time domain data would further be transformed into the frequency domain, where a perspective of the vibration signal in all frequency bands of interest is provided. To initiate this procedure, the motion vector processing module 130 projects the motion vector of each of the blocks onto multiple non-parallel axes (Step S208) and assigns a sign to each of the projected motion vectors (Step S210). Herein, the sign is either positive, negative, or zero depending upon the direction of the corresponding motion vector with respect to the referred axis. In other words, the motion vector of each block in the incoming frames would be projected onto different angle of axes, and the motion vector would be separate into a positive group, a negative group, and a zero group based on each angle of axis. The axes may be, for example, a 0-degree axis, a 45-degree axis, a 90-degree axis, and a 135-degree axis. The reason to employ multiple non-parallel axes is to avoid the movement of the breathing activity of the monitored subject being parallel to an only single axis, where in such case, the directions of all the corresponding motion vectors are difficult to be determined.

To be specific, assume that the axes include a first axis corresponding to a first angle and not being parallel to the central axis of the movement of the breathing activity of the monitored subject. The motion vector processing module 130 would project the motion vector of each block onto the first axis and determine an angle as well as a magnitude of the corresponding projected motion vector. The motion vector processing module 130 would assign either a positive sign, a negative sign, or zero to each projected motion vector on the basis of the range it falls into with respect to the first axis. The projected motion vector would be given a positive sign when its angle is between the first angle and (the first angle+$\pi$). The projected motion vector would be given a negative sign when its angle is between the first angle and (the first angle-$\pi$). The projected motion vector would be given zero when its angle is equal to the first angle or (the first angle±$\pi$). For example, say the first axis is a 45-degree axis, and the angles of a first projected motion vector and a second projected motion vector are respectively 60 degrees and 30 degrees. The first projected motion vector and the second projected motion vector would then be given a positive sign and a negative sign respectively.

After the signs of all projected motion vectors are determined, the waveform processing module 140 merges the projected motion vectors of each of the time series of incoming blocks with respect to each of the axes respectively into a corresponding 1D waveform (Step S212). To be specific, for each time series of incoming blocks with respect to each axis, the waveform processing module 140 would obtain the signs as well as the magnitudes of the projected motion vectors and thereby merge each of the projected motion vectors of the same time series of incoming blocks into a 1D waveform. Each 1D waveform corresponds to a time series of incoming blocks with respect to a referred axis. Namely, if each incoming frame is split into, say 64 blocks, there would be 64 1D waveforms with respect to each of the axes.

For better comprehension, the following diagrams would illustrate procedures to generate 1D waveforms from a time series of incoming frames according to an exemplary embodiment of the disclosure. The monitored subject herein is a sleeping infant.

Figure 3A:
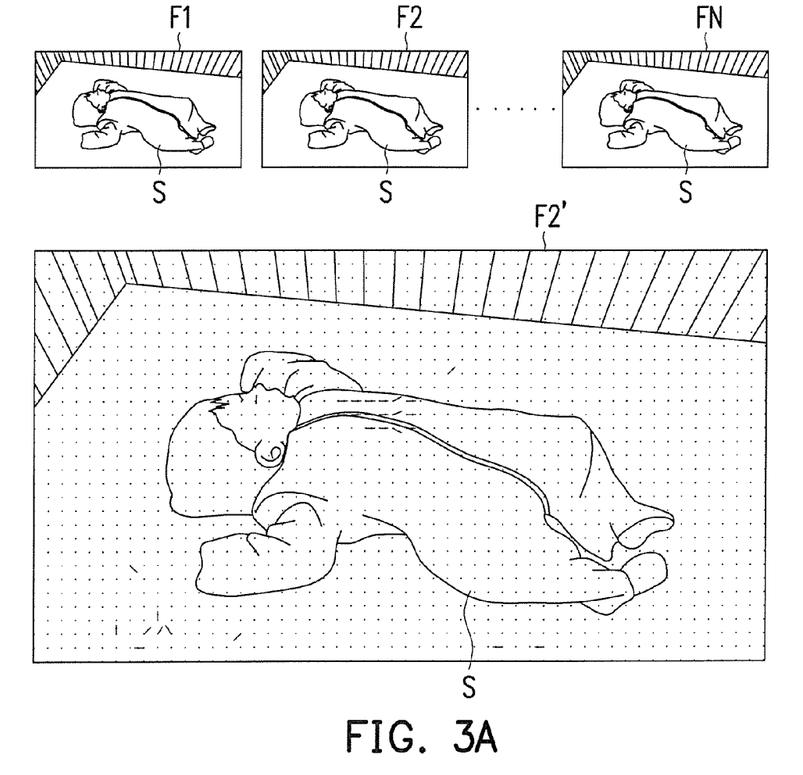
FIG. 3A illustrates a schematic diagram for computing motion vectors from two consecutive frames according to an exemplary embodiment of the disclosure.

FIG. 3A illustrates a schematic diagram for computing motion vectors from two consecutive frames according to an exemplary embodiment of the disclosure. After the image receiving module 110 obtains a time series of incoming frames F1~FN of a sleeping infant S and the image processing module 120 splits all the incoming frames F1~FN into equally-sized blocks, the motion vector processing module 130 would compute a motion vector of each block. For example, F2' illustrates the incoming frame F2 along with the motion vectors of all the blocks, where the motion vectors are computed based on the matching blocks between the frame F2 and its referenced frame F1.

Figure 3B:
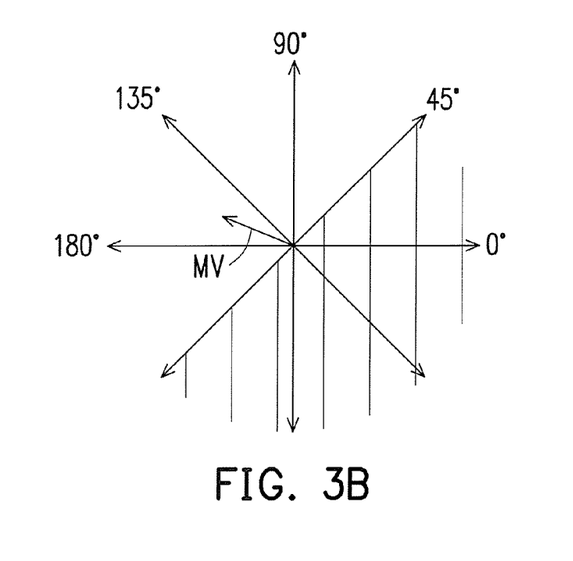
FIG. 3B illustrates a motion vector and multiple axes according to an exemplary embodiment of the disclosure.

Next, the motion vector processing module 130 would project the motion vectors onto multiple non-parallel axes. For example, FIG. 3B illustrates a motion vector and multiple axes according to an exemplary embodiment of the disclosure. Referring to FIG. 3B, a motion vector MV with an angle of 150° would be projected onto a 0° axis, a 45° axis, a 90° axis, and a 135° axis respectively. In terms of the 45° axis, any projected motion vector would be assigned a positive sign if its angle falls between 45° and 225° (i.e., the non-shaded part); any projected motion vector would be assigned a negative sign if its angle falls between 45° and −135° (i.e., the shaded part). Since the motion vector MV falls between 45° and 225°, it would be assigned a positive sign with respect to the 45° axis.

Figure 3C:
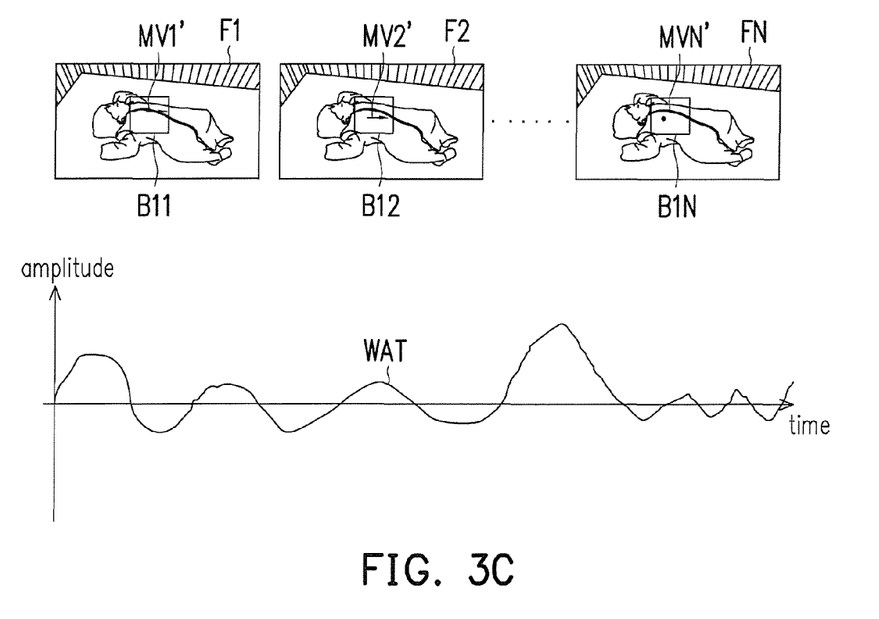
FIG. 3C illustrates a merged 1D waveform according to an exemplary embodiment of the disclosure.
Figure 3D:
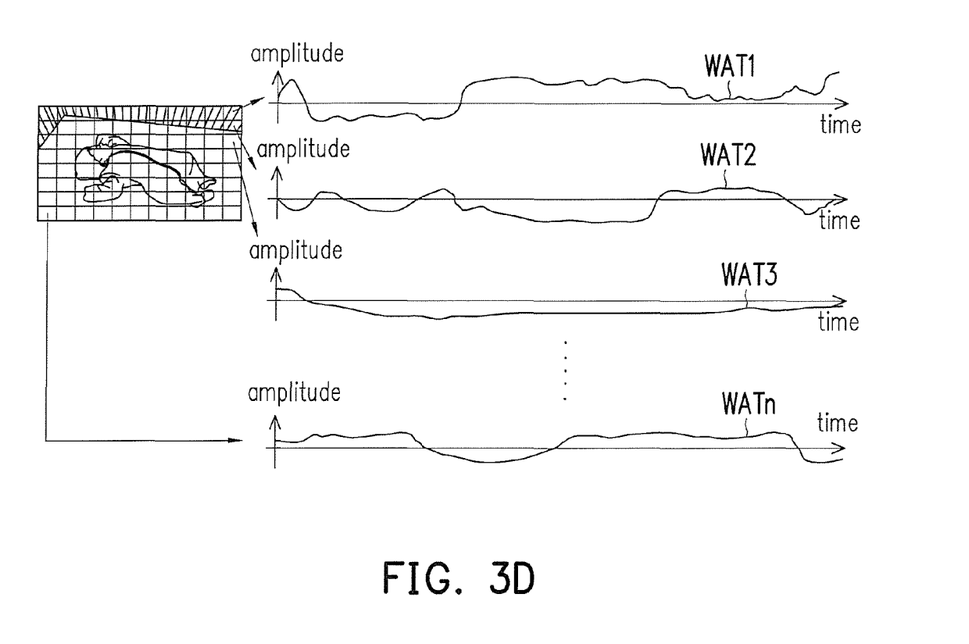
FIG. 3D illustrates a merged 1D waveform for each time series of incoming blocks according to an exemplary embodiment of the disclosure.

The waveform processing module 140 would merge the projected motion vectors of each of the time series of incoming blocks with respect to each of the axes into a corresponding 1D waveform. For example, FIG. 3C illustrates a merged 1D waveform according to an exemplary embodiment of the disclosure. Blocks B11~B1N are a time series of incoming blocks from the time series of incoming frames F1~FN. Assume that MV1'~MVN' are projected motion vectors with respect to the 45° axis. The waveform processing module 140 would merge the projected motion vectors MV1N'~MVN' into a waveform WAT. In other words, the waveform WAT is a 1D waveform that corresponds to the time series of incoming blocks B11~B1N with respect to the 45° axis. For a single axis, the waveform processing module 140 would merge the projected motion vectors for each time series of incoming blocks as illustrated in FIG. 3D. Referring to FIG. 3D, a waveform WAT1, a waveform WAT2, . . . , a waveform WATn correspond to each time series of incoming blocks with respect to the 45° axis. The same procedure would be performed by the waveform processing module 140 for other axes.

Revisiting FIG. 2, distinguished from a conventional approach to define an observe area which involves image recognition, the observe area locating module 150 defines the observe area in a frequency-based approach. Since the 1D waveforms are time domain data, the waveform processing module 140 would convert the 1D waveforms into the frequency domain (Step S214) through, for example, Fourier transformation, and the observe area locating module 150 would next locate an observe area associated with the monitored subject in the time series of incoming frames according to the converted 1D waveforms (Step S216).

The waveform processing module 140 would first perform frequency analysis on the converted waveform of each of the time series of incoming blocks with respect to each of the axes and thereby obtain a frequency analysis result corresponding to each of the axes, where each of the frequency analysis result includes frequency values corresponding to all the block positions. According to statistics, a newborn has a breathing rate of 40-44 per minute (i.e., 0.67-0.73 Hz); an infant aged under 1 year has a breathing rate of 30 per minute (i.e., 0.5 Hz); a child aged between 1-3 years has a breathing rate of 24 per minute (i.e., 0.4 Hz); a person aged above 10 years has a breathing rate of 12-20 per minute (i.e., 0.2 HZ). The above statistics could be set as a predefined principal breathing frequency range to find out an area which contains any vital sign information, and such area would be an observe area candidate. In other words, if there exist four axes, then there would be four observe area candidates. The observe area locating module 150 would determine an optimal frequency analysis result corresponding to only one of the axes (referred to as "an optimal axis" hereafter) and thereby locate the observe area according to the optimal frequency analysis result.

Figure 3E:
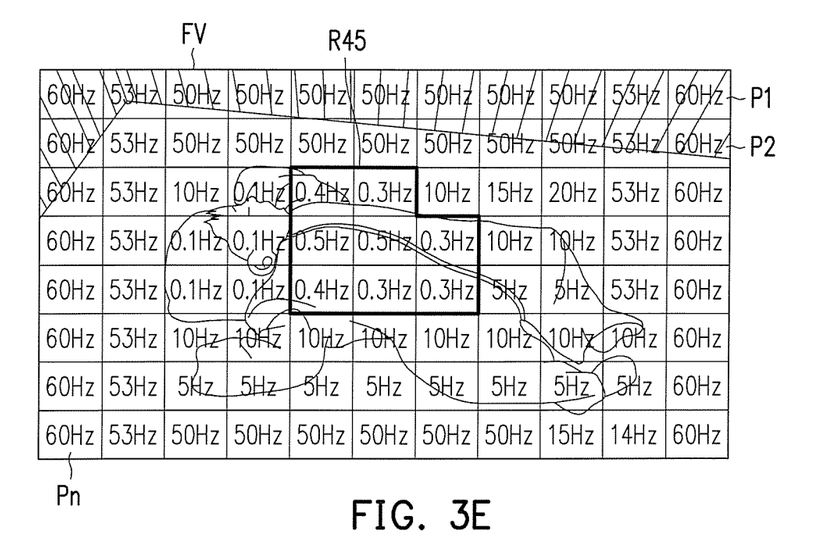
FIG. 3E illustrates a frequency analysis result according to an exemplary embodiment of the disclosure.

For example, FIG. 3E illustrates a frequency analysis result according to an exemplary embodiment of the disclosure. Referring to FIG. 3E, a frequency analysis result including multiple frequency values corresponding to block positions P1~Pn within a field of view FV is illustrated. It should be noted that, such result only correspond to a single axis, say, the 45° axis. In this instance, the predefined principal breathing frequency range could be set, for example, between 0.2 Hz and 0.73 Hz with a tolerance. The observe area locating module 150 would determine all observe area candidate blocks that form an observe area candidate by comparing the frequency analysis results with the predefined principal breathing frequency range. For example, the frequency value corresponding to block position Pk is 0.5 Hz which falls within the predefined principal breathing frequency range, and thus the block position Pk would be set as an observe area candidate block of the observe area candidate with respect to the 45° axis. In this case, the observe area locating module 150 would identify a region R45 with all the observe area candidate blocks as an observe area candidate.

Figure 3F:
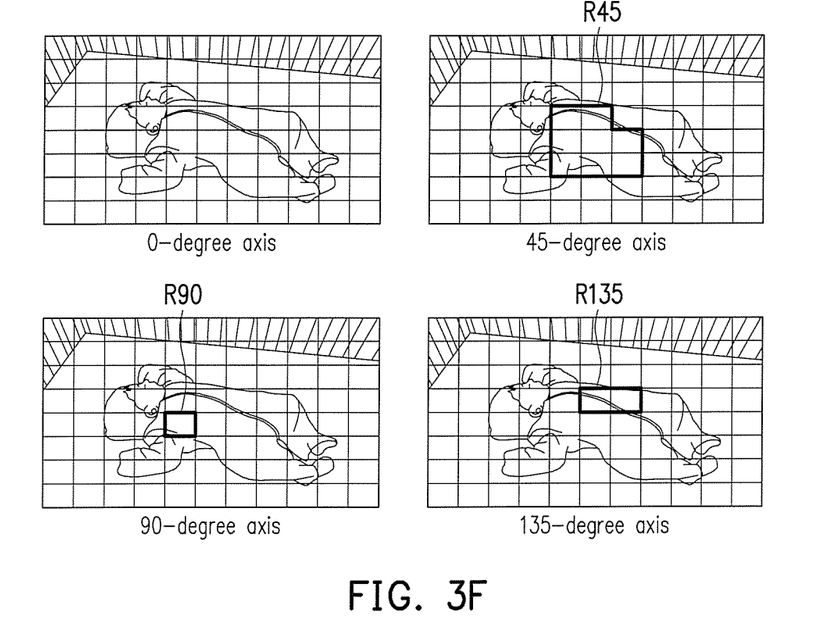
FIG. 3F illustrates four observe area candidates according to an exemplary embodiment of the disclosure.

Since there exist four axes (i.e., the 0° axis, the 45° axis, the 90° axis, and the 135° axis) in the present embodiment, the observe area locating module 150 would obtain four observe area candidates as illustrated in FIG. 3F. Referring now to FIG. 3F, regions R45, R90, and R135 respectively represent observe area candidates with respect to the 45° axis, the 90° axis, and the 135° axis. In the present embodiment, no observe area candidate is identified with respect to the 0° axis possibly due to its parallelism to the movement of the breathing activity of the monitored subject. Next, the observe area locating module 150 would sum up all the frequency values of the observe area candidate blocks within the observe area candidates and set the frequency analysis result of the observe area candidate with a maximum observe area frequency summation as the optimal frequency analysis result. In this instance, the region R45, which is around the chest and abdomen of the monitored subject, would be set as the observe area.

In an exemplary embodiment, the determination of the observe area would not only rely on the aforeillustrated principal frequency-amplitude distribution, but also on an area size. When the area of a located observe area is too small (i.e., not greater than a preset area threshold), this may be due to noise, motion artifact, or etc. In such instance, the observe area locating module could invalidate the located observe area.

Revisiting FIG. 2, after the observe area is located, the breathing frequency processing module 160 would determine a breathing frequency of the monitored subject corresponding to the observe area and thereby determine whether or not the monitored subject is breathing abnormally (Step S218). To be specific, the breathing frequency processing module 160 would superimpose the 1D waveforms for each of the time series of incoming blocks within the observe area with respect to the optimal axis so as to obtain a superimposed 1D waveform, and further convert the superimposed 1D waveform into the frequency domain so as to obtain the breathing frequency of the monitored subject.

Figure 3G:
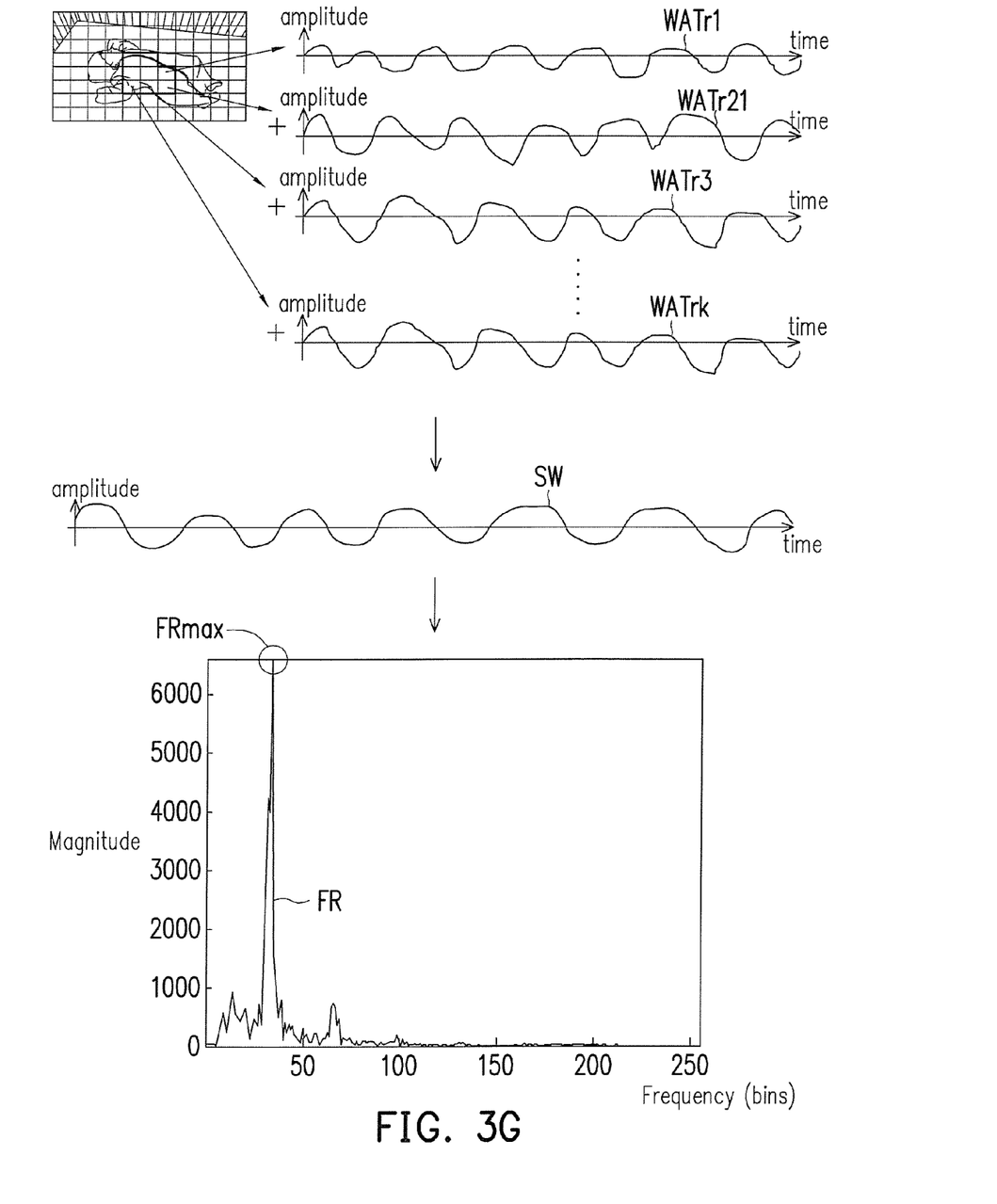
FIG. 3G illustrates a schematic diagram of the acquisition of a breathing frequency according to an exemplary embodiment of the disclosure.

FIG. 3G illustrates a schematic diagram of the acquisition of a breathing frequency according to an exemplary embodiment of the disclosure. Referring to FIG. 3G, since the region R45 corresponding to the 45° axis is the observe area, the breathing frequency processing module 160 would superimpose 1D waveforms WATr1, a waveform WATr2, . . . , a waveform WATrk corresponding to all time series of incoming blocks within the region R45 and a superimposed 1D waveform SW is formed thereafter. The superimposed 1D waveform SW would be further converted into the frequency domain and obtain frequency responses FR. The breathing frequency processing module 160 would extract a maximum frequency value FRmax from the frequency responses FR and consider it as the breathing frequency of the monitored subject within the time that the time series of incoming frames is received.

To determine the abnormality of the breathing activity, the breathing frequency corresponding to preceding time series of incoming frames would be continuously received and observed in a similar fashion. However, the optimal axis and the observe area would not be relocated within a certain time. In other words, the breathing frequency of the monitored subject within the same observe area in the preceding time series of incoming frames could be obtained via motion vector computation and projection, 1D waveform generation, superimposition, and conversion as previously described. The process would be repeated and the breathing frequency processing module 160 would determine whether the breathing frequency within the observe area meets an abnormal condition over a period of time. For example, if the breathing frequency falls out of the predefined principal breathing frequency range for over a period of time, the monitored subject is determined to be breathing abnormally.

In one exemplary embodiment, considering that the monitored subject would turn over while sleeping such that the position of chest and abdomen presented in the field of view of the image capturing device would be moved, the optimal axis could thus be redetermined and the observe area could be relocated every certain time.

In one exemplary embodiment, an alarm would be arranged at a distance from the monitored subject such that a caretaker of the monitored subject could perceive the alarm. The alarm could be wired or witlessly connected to the electronic device 100. Once the breathing frequency processing module 160 determines that the monitored subject is determined to be breathing abnormally, it would further transmit a signal to trigger the alarm so as to notify the caretaker that the breathing activity of the monitored subject is in potential jeopardy. For example, the alarm could be a monitoring bracelet worn by the caretaker that is witlessly connected to the electronic device 100. The breathing frequency processing module 160 would trigger the bracelet to generate a loud buzz, beep, or ring when the monitored subject is determined to be breathing abnormally.

Figure 4:
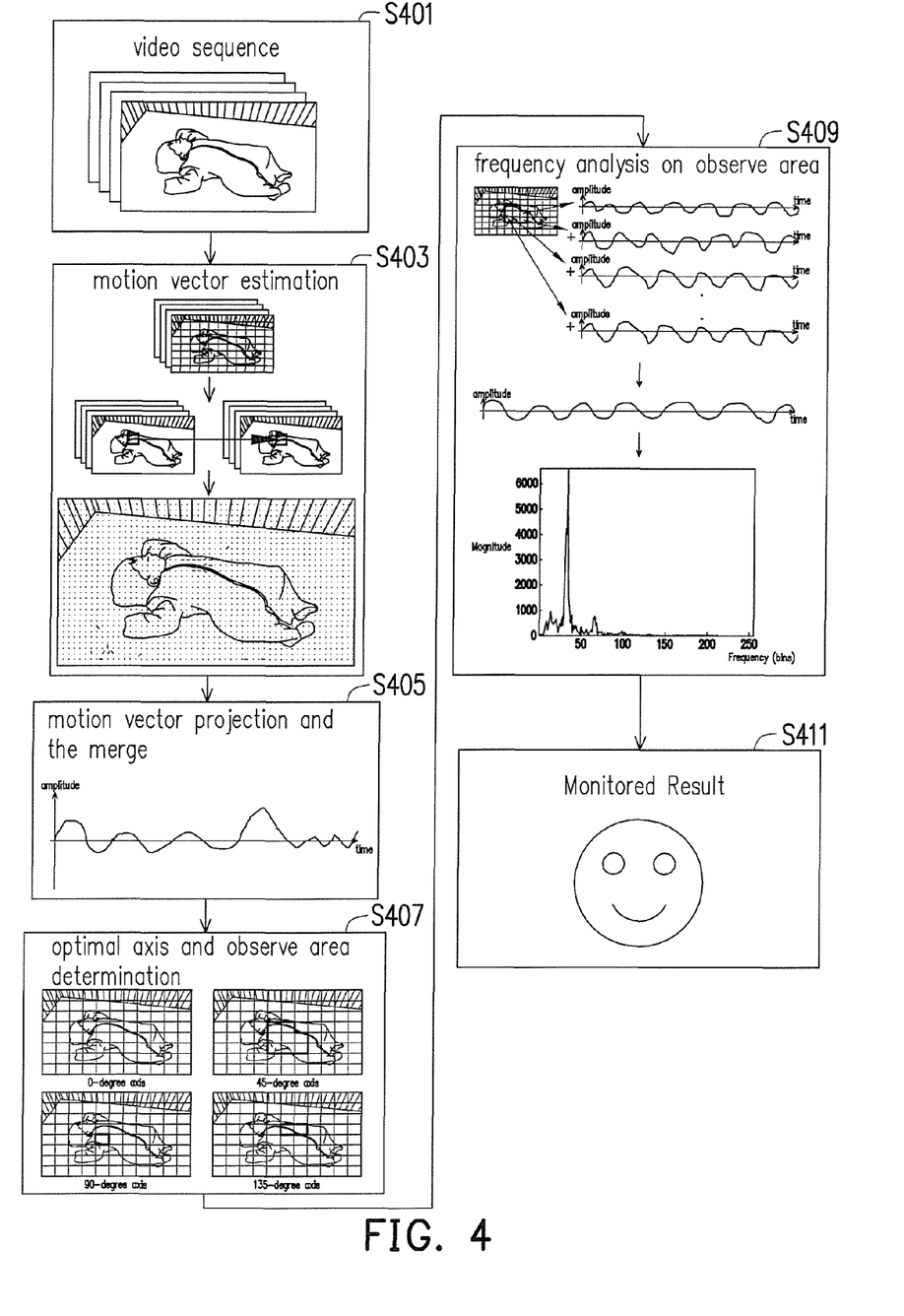
FIG. 4 illustrates functional block diagrams of a method for monitoring breathing activity in accordance with one of the exemplary embodiments of the disclosure.

The proposed method may be summarized in terms of functional block diagrams as illustrated in FIG. 4 in accordance with one of the exemplary embodiments of the disclosure. Referring to FIG. 4, the proposed method would first take in a video sequence (S401), and perform motion vector estimation of each block of each frame in the video sequence (S403). Next, the motion vectors of each block sequence would be projected and merged into a 1D waveform with respect to multiple non-parallel axes (S405). Observe area candidates corresponding to the axes which contain vital sign information would be determined by using a predefined principal frequency breathing range, and an optimal axis and an observe area would be selected based on its area size and principal frequency-amplitude distribution (S407). Next, frequency analysis would be performed on the observe area according to a video sequence continuously being received (S409), and the monitored result would be determined accordingly (S411).

The disclosure also provides a non-transitory computer-readable storage medium, which records computer program to be loaded into an electronic device to execute the steps of the aforementioned method. The computer program is composed of a plurality of program instructions (for example, an organization chart, establishing program instruction, a table approving program instruction, a setting program instruction, and a deployment program instruction, etc.), and these program instructions are loaded into the electronic device and executed by the same to accomplish various steps of the method for monitoring breathing activity of a subject.

In view of the aforementioned descriptions, the disclosure provides an image-based technique to monitor breathing activity of a subject through frequency analysis on the input video sequence. The disclosure not only obviates a need to put on any wearable device on the monitored subject, but also provides an approach to monitor breathing activity of a subject in a low-cost digital implementation and an efficient manner.

No element, act, or instruction used in the detailed description of disclosed embodiments of the present application should be construed as absolutely critical or essential to the present disclosure unless explicitly described as such. Also, as used herein, each of the indefinite articles "a" and "an" could include more than one item. If only one item is intended, the terms "a single" or similar languages would be used. Furthermore, the terms "any of" followed by a listing of a plurality of items and/or a plurality of categories of items, as used herein, are intended to include "any of", "any combination of", "any multiple of", and/or "any combination of multiples of the items and/or the categories of items, individually or in conjunction with other items and/or other categories of items. Further, as used herein, the term "set" is intended to include any number of items, including zero. Further, as used herein, the term "number" is intended to include any number, including zero.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A method for monitoring breathing activity, adapted to an electronic device, comprising:
    receiving a time series of incoming frames of a monitored subject and splitting each incoming frame in the time series of incoming frames into a plurality of blocks, wherein each of the blocks of the time series of incoming frames with a same block position forms a time series of incoming blocks;
    computing a motion vector of each of the blocks and projecting the motion vector of each of the blocks onto a plurality of non-parallel axes;
    assigning a sign to each of the projected motion vectors with respect to each of the axes, wherein the sign is either positive, negative, or zero;
    merging the projected motion vectors of each of the time series of incoming blocks with respect to each of the axes respectively into a corresponding one-dimensional (1D) waveform and converting the 1D waveforms into a frequency domain;
    locating an observe area associated with the monitored subject in the time series of incoming frames according to the converted 1D waveforms; and
    determining a breathing frequency of the monitored subject corresponding to the observe area and thereby determining whether or not the monitored subject is breathing abnormally.

2. The method according to claim 1, wherein after the step of receiving the time series of incoming frames of the monitored subject, the method further comprises:
    performing color transformation on the time series of incoming frames.

3. The method according to claim 1, wherein the axes comprise a first axis not parallel to a central axis of a movement of the breathing activity of the monitored subject, wherein the first axis corresponds to a first angle, and wherein the step of assigning the sign to each of the projected motion vectors with respect to each of the axes comprises:
    determining an angle of the projected motion vector;
    assigning the sign of the motion vector to zero when the angle of the projected motion vector is equal to the first angle or (the first angle±π);
    assigning the sign of the motion vector to positive when the angle of the projected motion vector is between the first angle and (the first angle+π); and
    assigning the sign of the motion vector to negative when the angle of the projected motion vector is between (the first angle−π) and the first angle.

4. The method of claim 3, wherein the step of merging the projected motion vectors of each of the time series of incoming blocks with respect to each of the axes respectively into the corresponding 1D waveform comprises:
    for each of the time series of incoming blocks with respect to each of the axes:
        obtaining magnitudes of the projected motion vectors; and
        merging each of the projected motion vectors of the time series of incoming blocks into the corresponding 1D waveform according to the magnitude and the sign.

5. The method of claim 1, wherein the step of locating the observe area associated with the monitored subject in the time series of incoming frames according to the converted 1D waveforms comprises:
performing frequency analysis on the converted waveform of each of the time series of incoming blocks with respect to each of the axes so as to obtain a corresponding frequency analysis result comprising a plurality of frequency values;
determining an optimal frequency analysis result with respect to an optimal axis among the axes; and
locating the observe area associated with the monitored subject in the time series of incoming frames according to the optimal frequency analysis result.

6. The method of claim 5, wherein the step of determining the optimal frequency analysis result with respect to the optimal axis among the axes comprises:
with respect to each of the axes:
determining whether the frequency value of a block position corresponding to each of the time series of incoming blocks is within a predefined principal breathing frequency range of the monitored subject; and
if yes, identifying the block position as an observe area candidate block; and
summing the frequency values of the candidate observe area blocks to obtain an observe area frequency summation; and
setting the observe area frequency summation with a maximum value as the optimal frequency analysis result, and setting the corresponding axis as the optimal axis.

7. The method of claim 6 further comprising:
determining whether an area of the located observe area is greater than an area threshold; and
if not, invalidating the located observe area.

8. The method of claim 5, wherein the step of determining the breathing frequency of the monitored subject corresponding to the observe area comprises:
superimposing the 1D waveforms with respect to the optimal axis for each of the time series of incoming blocks within the observe area so as to obtain a superimposed 1D waveform; and
converting the superimposed 1D waveform into the frequency domain so as to obtain the breathing frequency of the monitored subject.

9. The method of claim 1, wherein the step of determining whether or not the monitored subject is breathing abnormally comprises:
determining whether the breathing frequency of the monitored subject within the observe area meets an abnormal condition over a period of time, wherein the period of time corresponds to a plurality of preceding time series of incoming frames; and
if yes, determining that the monitored subject is breathing abnormally.

10. The method of claim 1, wherein when the monitored subject is determined to be breathing abnormally, the method further comprises:
triggering an alarm connected to the electronic device.

11. An electronic device comprising:
a memory, recording a plurality of modules; and
a processor, coupled to the memory, and accessing and executing the modules recorded in the memory, wherein the modules comprise:
an image receiving module, receiving a time series of incoming frames of a monitored subject;
an image processing module, splitting each incoming frame in the time series of incoming frames into a plurality of blocks, wherein each of the blocks of the time series of incoming frames with a same block position forms a time series of incoming blocks;
a motion vector processing module, computing a motion vector of each of the blocks, projecting the motion vector of each of the blocks onto a plurality of non-parallel axes, and assigning a sign to each of the projected motion vectors with respect to each of the axes, wherein the sign is either positive, negative, or zero;
a waveform processing module, merging the projected motion vectors of each of the time series of incoming blocks with respect to each of the axes respectively into a corresponding one-dimensional (1D) waveform and converting the 1D waveforms into a frequency domain;
an observe area locating module, locating an observe area associated with the monitored subject in the time series of incoming frames according to the converted 1D waveforms;
a breathing frequency processing module, determining a breathing frequency of the monitored subject corresponding to the observe area and thereby determining whether or not the monitored subject is breathing abnormally.

12. The electronic device according to claim 11, wherein the image processing module further performs color transformation on the time series of incoming frames.

13. The electronic device according to claim 11, wherein the axes comprise a first axis not parallel to a central axis of a movement of the breathing activity of the monitored subject, wherein the first axis corresponds to a first angle, and wherein the motion vector processing module determines an angle of the projected motion vector, assigns the sign of the motion vector to zero when the angle of the projected motion vector is equal to the first angle or (the first angle$\pm\pi$), assigns the sign of the motion vector to positive when the angle of the projected motion vector is between the first angle and (the first angle$+\pi$), and assigns the sign of the motion vector to negative when the angle of the projected motion vector is between (the first angle$-\pi$) and the first angle.

14. The electronic device according to claim 13, wherein for each of the time series of incoming blocks with respect to each of the axes, the waveform processing module obtains magnitudes of the projected motion vectors and merges each of the projected motion vectors of the time series of incoming blocks into the corresponding 1D waveform according to the magnitude and the sign.

15. The electronic device according to claim 11, wherein the waveform processing module performs frequency analysis on the converted waveform of each of the time series of incoming blocks with respect to each of the axes so as to obtain a corresponding frequency analysis result comprising a plurality of frequency values, and wherein the observe area locating module determines an optimal frequency analysis result with respect to an optimal axis among the axes and locates the observe area associated with the monitored subject in the time series of incoming frames according to the optimal frequency analysis result.

16. The electronic device according to claim 15, wherein with respect to each of the axes:
the observe area locating module determines whether the frequency value of a block position corresponding to each of the time series of incoming blocks is within a predefined principal breathing frequency range of the monitored subject;

if yes, the observe area locating module identifying the block position as an observe area candidate block; and the observe area locating module sums the frequency values of the candidate observe area blocks to obtain an observe area frequency summation; and wherein the observe area locating module sets the observe area frequency summation with a maximum value as the optimal frequency analysis result, and setting the corresponding axis as the optimal axis.

17. The electronic device according to claim 16, wherein the observe area locating module further determines whether an area of the located observe area is greater than an area threshold, and wherein if not, the observe area locating module invalidates the located observe area.

18. The electronic device according to claim 11, wherein the breathing frequency processing module superimposes the 1D waveforms with respect to the optimal axis for each of the time series of incoming blocks within the observe area so as to obtain a superimposed 1D waveform, converts the superimposed 1D waveform into the frequency domain so as to obtain the breathing frequency of the monitored subject, and determines whether the breathing frequency of the monitored subject within the observe area meets an abnormal condition over a period of time, and wherein if yes, the breathing frequency processing module determines that the monitored subject is breathing abnormally, wherein the period of time corresponds to a plurality of preceding time series of incoming frames.

19. The electronic device according to claim 11, wherein the breathing frequency processing module further triggers an alarm connected to the electronic device when the monitored subject is determined to be breathing abnormally.

20. A non-transitory computer-readable storage medium, storing programs to be loaded into an electronic device to perform steps of:

receiving a time series of incoming frames of a monitored subject and splitting each incoming frame in the time series of incoming frames into a plurality of blocks, wherein each of the blocks of the time series of incoming frames with a same block position forms a time series of incoming blocks;

computing a motion vector of each of the blocks and projecting the motion vector of each of the blocks onto a plurality of non-parallel axes;

assigning a sign to each of the projected motion vectors with respect to each of the axes, wherein the sign is either positive, negative, or zero;

merging the projected motion vectors of each of the time series of incoming blocks with respect to each of the axes respectively into a corresponding one-dimensional (1D) waveform and converting the 1D waveforms into a frequency domain;

locating an observe area associated with the monitored subject in the time series of incoming frames according to the converted 1D waveforms; and determining a breathing frequency of the monitored subject corresponding to the observe area and thereby determining whether or not the monitored subject is breathing abnormally.

* * * * *